United States Patent [19]

Iskra

[11] Patent Number: 4,559,050
[45] Date of Patent: Dec. 17, 1985

[54] THIN, SOFT, ABSORBENT PRODUCT
[75] Inventor: Michael J. Iskra, Flemington, N.J.
[73] Assignee: Personal Products Company, Milltown, N.J.
[21] Appl. No.: 641,545
[22] Filed: Aug. 17, 1984
[51] Int. Cl.⁴ .............................................. A61F 13/00
[52] U.S. Cl. .................................... 604/368; 604/379
[58] Field of Search ............... 604/367, 368, 374, 375, 604/379, 378, 380–383, 385

[56] References Cited

U.S. PATENT DOCUMENTS

| Re. 26,151 | 1/1967 | Duncan et al. | 604/379 |
|---|---|---|---|
| 2,788,003 | 4/1957 | Morin | 604/379 |
| 4,102,340 | 7/1978 | Mesek et al. | 604/379 |
| 4,186,165 | 1/1980 | Aberson et al. | 604/379 |
| 4,340,057 | 7/1982 | Bloch et al. | 604/379 |
| 4,500,315 | 2/1985 | Pieniak et al. | 604/379 |

Primary Examiner—John D. Yasko
Attorney, Agent, or Firm—Martha A. Michaels

[57] ABSTRACT

An absorbent structure is provided, which is comprised of a fibrous web, having an initial dry bulk of at least about 20 cc/gm., a dry bulk recovery of at least about 30 percent, and a wet bulk of at least about 30 cc/gm., and a basis weight less than about 4 oz/sq. yd. containing at least about 200 percent by weight superabsorbent. The structure is microcorrugated to provide a softness having a Taber stiffness value less than about 50.

10 Claims, 11 Drawing Figures

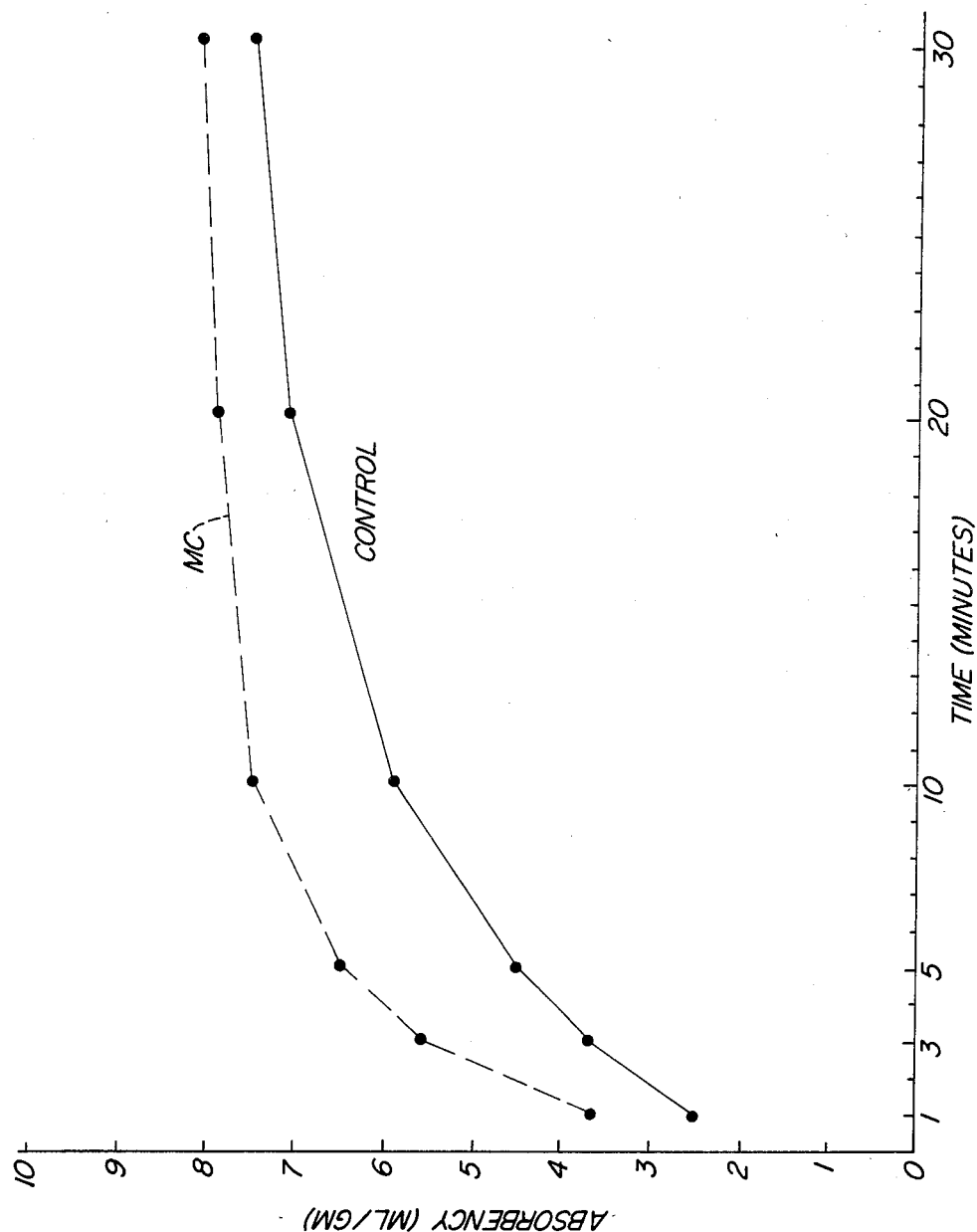

THIN, SOFT, ABSORBENT PRODUCT

BACKGROUND OF THE INVENTION

The present invention relates to new and improved thin, soft, absorbent products, and more particularly, to new and improved soft compressed composites incorporating superabsorbent material and which absorb large quantities of liquids.

Disposable absorbent products have been known for some time, including such products as disposable diapers, sanitary napkins, wound dressings, bandages, incontinent pads, and the like. These products incorporate an absorbent batt which is used to absorb and hold or contain body fluids. Initially, in many of these products, especially diapers and sanitary napkins, the absorbent batt comprised what is termed "wadding" or plies of tissue. The wadding was disposed between an impermeable backing and a permeable facing and the plies of tissue were used to absorb and, hopefully, contain the liquid within the product. A diaper which utilizes such an absorbent batt is disclosed in U.S. Pat. Re. No. 26,151.

The wadding type of batt was replaced, for the most part, by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also the fluffed wood pulp layer is quite soft, flexible and conformable and hence, produces an improved diaper over diapers using wadding as the absorbent layer.

Though the fluffed wood pulp absorbent batts have improved capacity, the efficiency with which the capacity is used in a diaper or sanitary napkin is poor. The reason for this, is that the fluid to be absorbed is generally deposited in a localized area within the absorbent batt and the ability for the fluid to move along the plane of the batt is poor. The fluid follows the path of least resistance and consequently moves to the closest edge of the batt where it generally is no longer contained and the product leaks. Furthermore, the wood pulp batts lack stability, e.g., when a diaper is being worn, the batt tends to break up creating bunching.

U.S. Pat. No. 3,017,304 discloses an absorbent product which incorporates in the product a densified, paper-like layer. This paper-like layer acts as a wick, i.e., liquid which is placed on the layer tends to move rapidly along the plane of the layer. When incorporated in combination with fluffed wood pulp fiber, the resultant product uses the absorbent capacity of the fluffed wood pulp much more efficiently. Diapers which incorporate this paperlike layer combined with fluffed wood pulp are disclosed and described in U.S. Pat. Nos. 3,612,055 and 3,938,522. This concept of combining a wicking layer or capillary skin with fluffed wood pulp fibers has gained wide acceptance in many absorbent products including disposable diapers and sanitary napkins. Even though these products make much greater use of the capacity of the absorbent batt, they still do not totally contain the absorbed liquid. It is probable that these products will leak before the full capacity of the batt is used for absorption. This is especially true if pressure is placed on the batt while wet, for example a baby sitting down on a previously wetted diaper will very often cause the batt to leak. Although the batt is somewhat stabilized by the paper-like densified skin, it may crack and separate.

Recently, elastic leg diapers or stretch diapers have been introduced into the marketplace. Though these diapers provide no better absorbent batt than flat diapers or the prior art diapers, they have indicated improved containment of liquid. Such diapers are disclosed and described in U.S. Pat. Nos. 3,860,003, 4,050,462, and 4,324,245. Though the containment features are better than the prior art products, the elasticized products fit more tightly permitting less air circulation. Frequently, this can become irritating to the skin and the tighter the elastic or the more close fitting the diaper, the greater the irritation. This is especially true adjacent the area where the elastic leg portion of the product contacts the wearer.

A number of years ago "superabsorbent materials", i.e., materials which will absorb many times their weight of liquid, were developed. Since the development of such materials, people have been trying to incorporate them in absorbent products such as diapers and sanitary napkins to enhance the absorptive performance of these products. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a liquid-permeable facing and a liquid-impermeable backing sheet. The absorbent layer contains water insoluble cross-linked hydrocolloid polymer as the superabsorbent material.

Even though superabsorbent materials have been available for some time, they have not gained wide acceptance in absorbent products such as disposable diapers and sanitary napkins. A primary reason for this lack of acceptance of the superabsorbents is failure to develop a product capable of economically utilizing the highly increased absorptive capacity of the superabsorbent material. In order to economically utilize a superabsorbent, the liquid being absorbed must be transported to the superabsorbent material. In other words, the superabsorbent material must be placed in contact with the liquid. Furthermore, as the superabsorbent material absorbs the liquid, it must be allowed to swell. If the superabsorbent is prevented from swelling, it will cease absorbing liquid. Hence if the superabsorbent material is to function in diapers and sanitary napkins wherein the liquid to be absorbed is placed in a small void area, the structure of the absorbent layer containing superabsorbent materials appears to be critical. Over the years a number of techniques have been disclosed in an attempt to provide structures which make efficient use of the superabsorbent material. Such products are disclosed in U.S. Pat. Nos. 4,103,062, 4,102,340, and 4,235,237. In addition, methods for incorporating superabsorbents into suitable layers or suitable configurations which can be placed in an absorbent product, are disclosed in U.S. Pat. Nos. 4,186,165, 4,340,057 and 4,364,992. To date, none of these products has met with any substantial commercial success.

In copending Application Ser. No. 439,963, filed Nov. 8, 1982, a particularly useful compressed composite is formed. This application is hereby incorporated by reference. The compressed composite product is preferably made from nonwoven fabric such as polyester. The fabric has associated with it at least 200 percent by weight of superabsorbent to form an absorbing layer. In order to provide a product which will not only absorb liquid but also transport liquid, wood pulp fibers or other suitable wicking materials are cast in a layer on at least one side of the absorbing layer. The product is then compressed to yield a very high liquid absorbing product. However, the resulting compressed composite is quite stiff, and hence requires softening to provide flexibility for utilization in products such as diapers and the like. The flexibility provided needs to be permanent, i.e., the surrounding environment, handling of the product, and its subsequent use will not affect the softness and flexibility.

The present invention provides a new and improved absorbent composite structure which utilizes a substantial portion of the absorptive capacity of superabsorbent materials and yet is soft and flexible. This soft, flexible composite makes use of the capacity of the superabsorbent materials. Furthermore, the composite retains its substantially completely stable state though rendered soft and flexible. Whether wet or dry, the composite does not break, bunch or separate. The soft composite retains absorbed liquid without yielding any of the liquid when the composite is under pressure.

SUMMARY OF THE INVENTION

The present invention provides an absorbent composite structure which is comprised of a fibrous web and superabsorbent. The fibrous web contains the superabsorbent, disposed in amongst the fibers of the web, in an amount of at least about 200 percent by weight based on the web weight. The absorbent structure is rendered flexible to possess a Taber stiffness value of about 25 or less.

One use of the absorbent structure is as the absorbing layer of the compressed composite product discussed above. The fibrous web used as a basis for the absorbing layer is preferably a low density, resilient, fibrous web consisting of randomly disposed fibers which result in a web having a dry bulk recovery of at least 30 percent, an initial dry bulk of at least 20 cc/gm., a wet bulk of at least 30 cc/gm., and a weight less than about 4 oz/sq. yd., preferably less than, 3 oz/sq. yd. The fibrous web is used to spacially distribute superabsorbent material so that upon exposure to an aqueous fluid, swelling occurs with minimal interference from adjacent superabsorbent material. The resulting absorbing layer which, due to the high loading of superabsorbent, is too stiff for most uses can be softened to a Taber stiffness of about 25 or less as it is, or after a transporting or wicking layer of a higher density material is superimposed upon the absorbing layer and the layers are compressed. The compressed composite product in accordance with the present invention can be softened to a Taber stiffness of about 25 or less.

The present invention also includes a method for preparing a soft, flexible, absorbent structure. A nonwoven web of synthetic, wet resilient fibers containing at least about 200 percent by weight of superabsorbent is dried to a moisture content of less than about 25 percent, preferably less than about 10 percent, and microcorrugated to provide a Taber stiffness value less than about 25. The microcorrugating process consists of passing the web through fluted intermeshing rolls having sufficient pressure to fracture the superabsorbent and form cross-directional hinge lines. Subsequently, the web can be passed through an embossing roll with rings set to fracture the superabsorbent and place lines in the product in a machine direction, thus providing hinge lines in the machine direction.

BRIEF DESCRIPTION OF THE DRAWINGS

FIG. 10 is a graph depicting the test results of Example 2.

DETAILED DESCRIPTION OF THE PRESENT INVENTION

Figure 1:
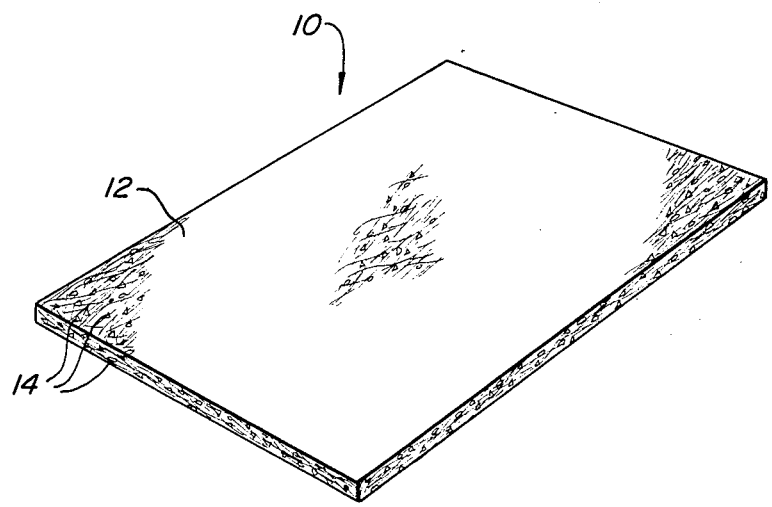
FIG. 1 is a perspective view illustrating one type of starting material for the present invention.

Referring now to the drawings, FIG. 1 represents a perspective view of starting material utilized to make the absorbent product of the present invention. The starting material 10 is a fibrous web containing at least about 200 percent superabsorbent by weight of the web. The superabsorbent particles 14 are distributed substantially throughout the web 12.

Figure 2:
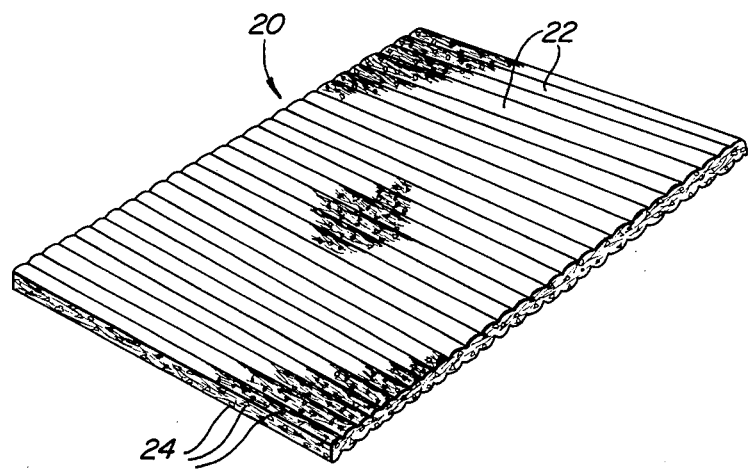
FIG. 2 is a perspective view of one embodiment of the present invention.

FIG. 2 denotes a fibrous web 20 which contains superabsorbent material 24. The fibrous web 20 has been microcorrugated to provide microcorrugations 22 in the fibrous web resulting in a softness and flexibility imparted to an otherwise stiff material.

Figure 3:
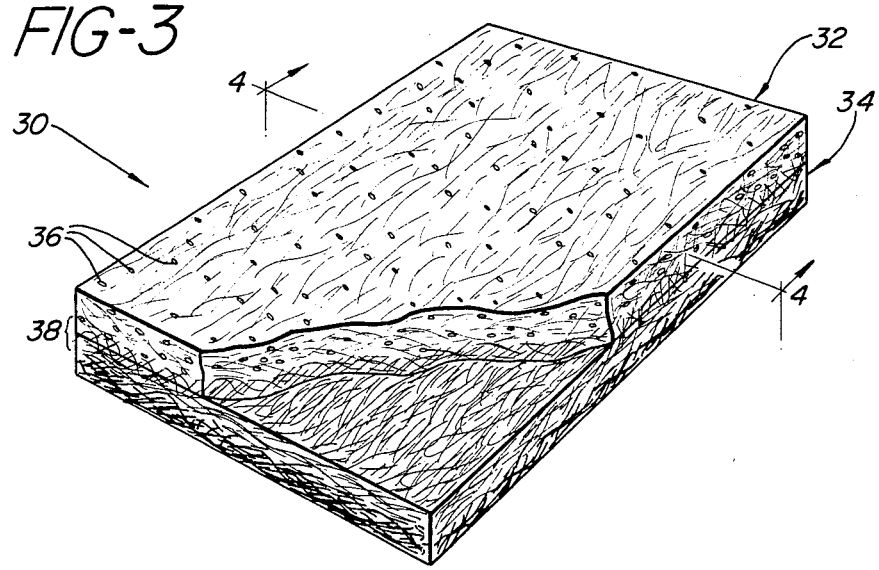
FIG. 3 is a perspective view of another type of starting material for use in the present invention.

FIG. 3 represents a perspective view of another starting material for the absorbent structure of the present invention. The starting material 30 has a fibrous web as an absorbing layer 32. Interspersed and fixed in the absorbing layer, is superabsorbent material 36. Immediately associated with the absorbing layer is a wicking layer 34. Some portions of the wicking layer 34 extend into and become integral with the absorbing layer 32 thus forming a transition zone 38. By "integral with" is meant in intimate contact with but not requiring physical or chemical bonding. The structure depicted in FIG. 3 is in an uncompressed state for ease of illustration. Upon compression, some of the portions in the wicking layer 34 will extend into and become integral with the fibers of the absorbing layer. These wicking layer portions consequently will also be in contact with the superabsorbent material. Generally, at least 10 percent moisture is present when the structure is compressed under a pressure sufficient to compact the structure and cause the softened surface of the superabsorbent material to provide the necessary adhesion to the fibers of the absorbing layer so that the composite remains in a compacted state even when dry.

Figure 4:
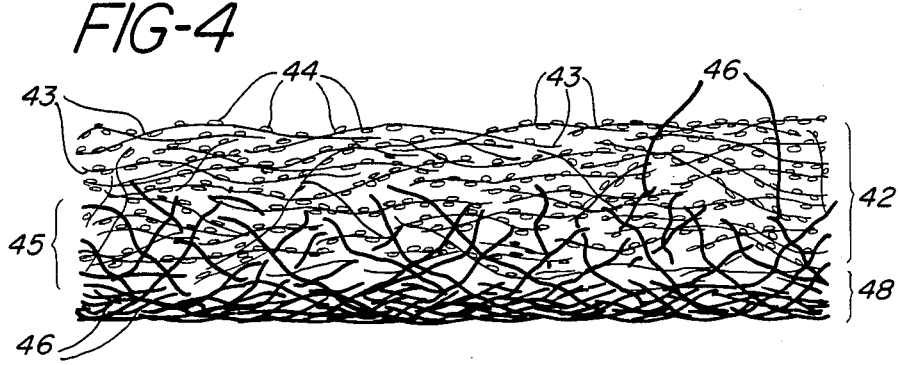
FIG. 4 is an enlarged cross-sectional view along lines 4—4 of FIG. 3.

FIG. 4 provides a cross-sectional view along line 4—4 of FIG. 3 showing in detail the relationship of the layers of the starting material. The absorbing layer 42 is generally made from resilient staple fibers. The superabsorbent material 44 is interspersed and preferably fixed among the resilient fibers 43. The wicking layer 48 is comprised of portions 46, some of which extend into and become integral with the absorbing layer. The transition zone 45 contains the wicking layer portions 46 in contact with the portion of the absorbing layer 42 and its fibers 43 so as to be in intimate contact with some of the superabsorbent particles 44.

Figure 4A:
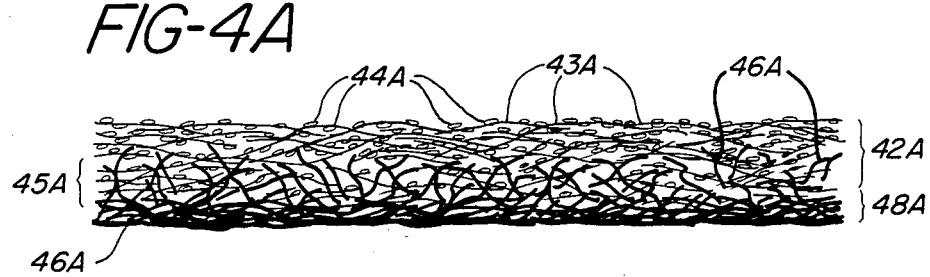
FIG. 4A is an enlarged cross-sectional view along lines 4—4 of FIG. 3 after compression.

FIG. 4A depicts the structure of FIG. 4 in a compressed state showing that the absorbing layer 42A has been substantially reduced in thickness and the wicking layer 48A has also been reduced in thickness but extends considerably into and becomes integral with the absorbing layer to form a transition zone 45A. Although the super-absorbent particles 44A are closer to each other, there is still sufficient opportunity for liquid to pass between the particles and upon their softening the resilient fibers of the absorbing layer are released to return the layer to its original low density form. The compressed product depicted in FIG. 4A is substantially stiff and may have a Taber stiffness of at least about 300 in the machine direction.

Figure 5:
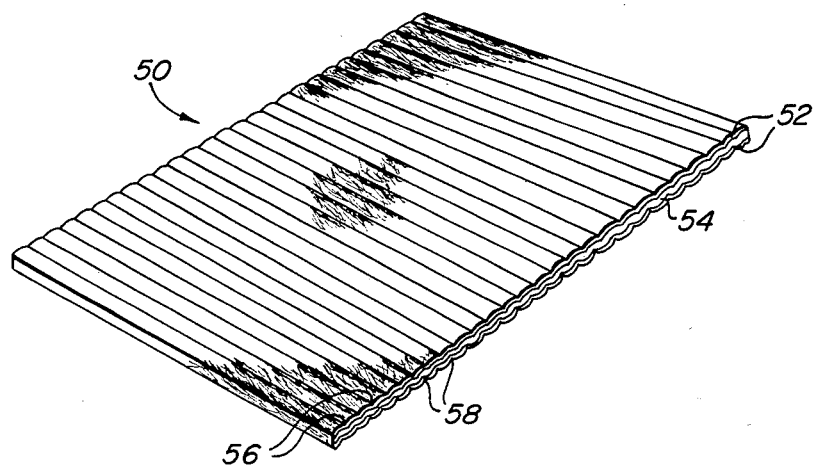
FIG. 5 is a perspective view of one embodiment of the present invention.

FIG. 5 is a perspective view of an absorbent structure of the present invention, namely that of FIG. 4A, which has been microcorrugated. The structure 50 contains wicking layers 52, an absorbing layer 54, and microcorrugation hinge lines 56 and 58 which provide a Taber stiffness less than 25 in at least one direction.

Figure 6:
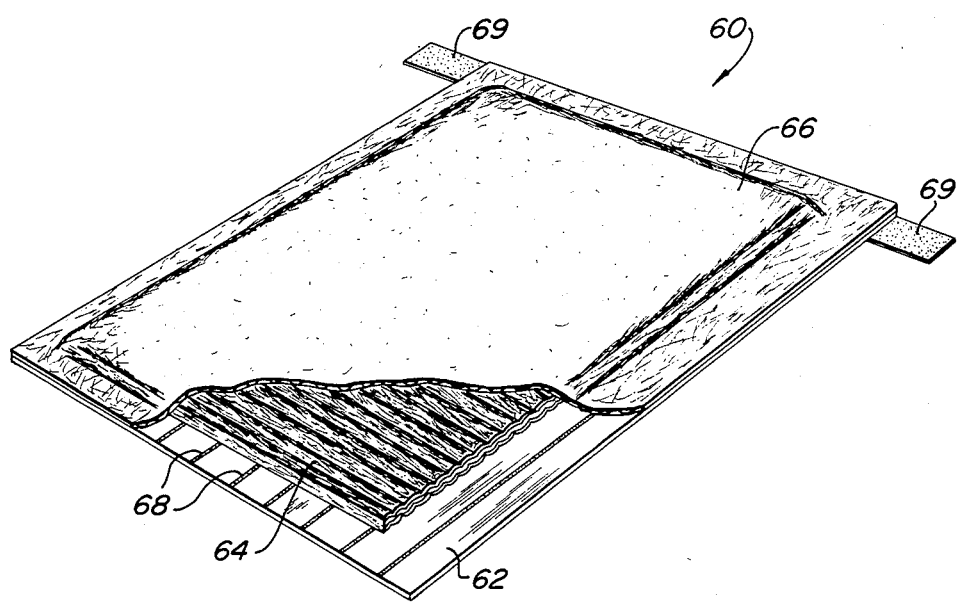
FIG. 6 is a perspective view of another embodiment of the present invention.

FIG. 6 depicts a disposable diaper 60 utilizing an absorbent structure of the present invention. A portion of the drawing is broken away for clarification. The disposable diaper 60 has a liquid-permeable facing 66 and a liquid-impermeable backing 62. In between the facing 66 and backing 62 is an absorbent structure 64. The structure has wicking layers, a transition zone, and an absorbing layer as described for the products of FIGS. 3 and 4. The absorbent structure 64 is held in place by glue lines 68 so that it is sandwiched between the facing 66 and the backing 62. Tape tabs 69 are affixed to two corners of the diaper product in order to fasten the product about the waist of the wearer.

Figure 7:
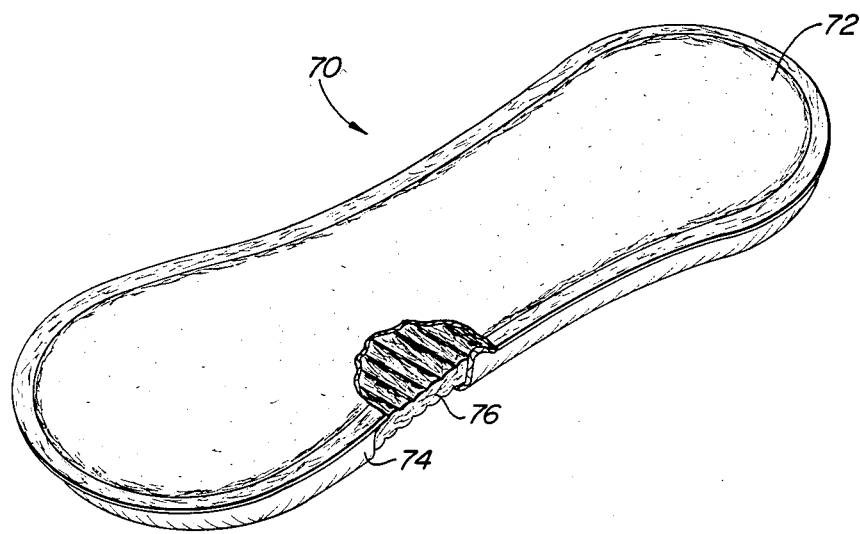
FIG. 7 is a perspective view of a still further embodiment of the present invention.

FIG. 7 is a perspective view of a sanitary napkin 70. The napkin is comprised of a liquid-impermeable shell 74 which contains an absorbent structure 76 and is covered over the upper surface with a liquid-permeable facing 72. The absorbent structure 76 is made in accordance with the present invention and is similar to that of FIG. 5.

Figure 8:
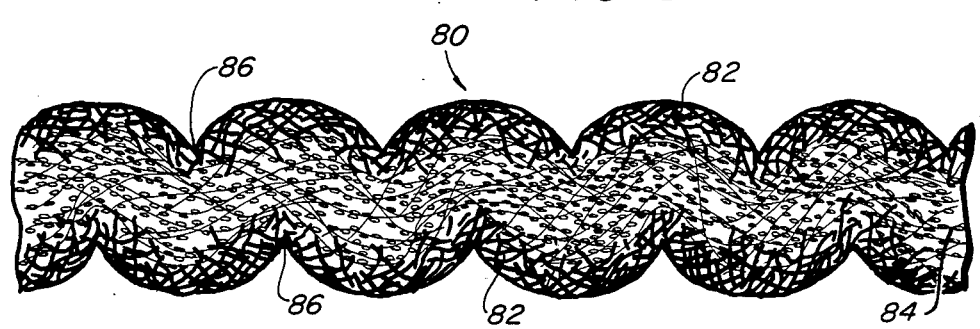
FIG. 8 is an enlarged side elevational view of a portion of the embodiment shown in FIG. 5.

FIG. 8 is an enlarged side elevational view showing a portion of the absorbent structure of FIG. 5 in more detail. The absorbent structure 80 is comprised of wicking layers 82 placed on each side of an absorbing layer 84. Generally, the superabsorbent material is polymerized from a monomer while the monomer is in contact with the fibers of the absorbing layer 84. Whenever a monomer is polymerized on a fibrous web such as the absorbing layer 84, it tends to polymerize in large globules or film-like pieces at the interstices of the web fibers. This adheres tee fiber-crossovers to each other resulting in a stiffness imparted to the fibrous web. When the stiff web is subjected to microcorrugating, the superabsorbent polymer is reduced in size by fracturing to create a network of substantially parallel hinge lines no more than ¼ inch apart. The principle is to break-up the superabsorbent material without materially damaging the original fiber matrix of the fibrous web. In other words, the web is rendered flexible and soft without a substantial loss of tensile strength.

Figure 9:
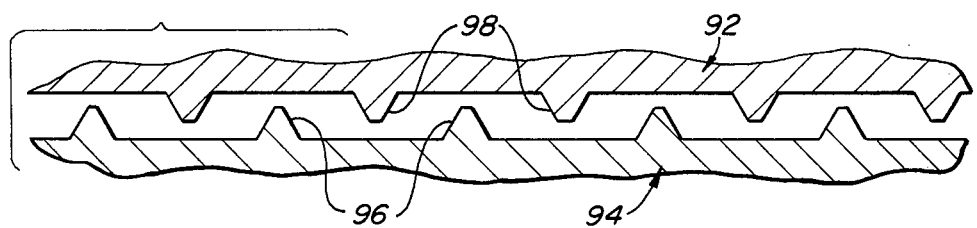
FIG. 9 is an enlarged side elevational view of a portion of the microcorrugating rolls.

FIG. 9 depicts an enlarged side elevational view of a portion of suitable microcorrugating rolls. The rolls 92 and 94 possess flutes 96 and 98 which intermeshed as the rolls rotate in opposite directions. The flutes 96 and 98 create staggered parallel cross directional lines in the absorbent structure creating hinge lines which impart flexibility without substantially damaging the integrity and functionality of the structure.

FIG. 10 is a graph comparing the rate of absorbency of an absorbent structure which has been microcorrugated (MC) to an absorbent structure (control) which has not been treated. The graph clearly shows that an absorbent structure which has been microcorrugated absorbs liquid much more rapidly than the control.

These and other products, such as incontinent pads, wound dressings, and the like, may be made from the absorbent structures depicted in the drawings.

The fibrous web which contains the superabsorbent and forms the basic absorbing layer for the absorbent structure of the present invention is of substantially high loft and upon dry compression followed by release has a tendency to return substantially to its original thickness. For instance, fibrous webs formed from synthetic staple fibers, such as polyethylene, polypropylene, polyester, nylon, bicomponent fibers, and the like, are particularly desirable. Melt blown fibrous webs also are suitable. However, cellulosic fibers such as rayon may be used. Generally, the fibers are air-laid or melt-blown to form a web, which if needed, is then stabilized. Stabilization may be achieved by heat-through bonding, adhesive bonding, point embossing with heat or adhesive, and the like. The stabilizing process is selected according to the fibers used and the process used to form the web. Suitable procedures for forming a web include carding, wet-laying, air-laying, or combinations of these, melt blowing and other suitable known techniques. The fibrous web preferably has a dry bulk recovery of at least about 30 percent, an initial dry bulk of at least about 20 cc/gm., and a wet bulk of at least about 30 cc/gm. The fabric has a weight of less than about 4 oz/sq. yd.

In one embodiment, a blend of staple polyester fibers with a minor portion of fusible fibers, are air-laid to form a web. The web is subsequently lightly bonded by passing hot air through the fibers making the fusible fibers tacky so as to stick to each other and the staple fibers to provide some degree of integrity to the web structure.

The superabsorbent material present in an intermittently dispersed form in the absorbing layer is generally a water-insoluble but water-swellable polymeric substance capable of absorbing water in an amount which is at least 10 times the weight of the substance in its dry form. The superabsorbent material is in the form of particles which may be in the shape of fibers, spheres, bits of film, globules, or the like, or may be applied in the form of a liquid monomer solution which is subsequently polymerized. Generally, the polymerized monomer solution provides globules and bits of film-like particles in the structure.

In one type of superabsorbent material, the particles or fibers may be described chemically as having a backbone of natural or synthetic polymers with hydrophilic groups or polymers containing hydrophilic groups being chemically bonded to the backbone or an intimate admixture therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula

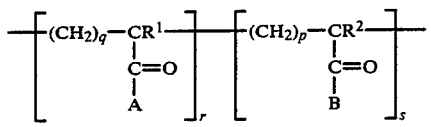

wherein A and B are selected from the group consisting of $-OR^3, -O$ (alkali metal), $-OHNH_3, -NH_2$, wherein $R^1$, $R^2$ and $R^3$ are selected from the group consisting of hydrogen and alkyl having 1 to 4 or more carbon atoms, wherein r is an integer having a value of 0 to about 5000 or more, s is an integer having a value of 0 to about 5000 or more, r plus s is at least 500, p is an integer having a value of zero or 1 and q is an integer having a value of 1 to 4. The preferred hydrophilic chains are hydrolyzed polyacrylonitrile chains and co-polymers of polyacrylamide and polysodium acrylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly(N-N-dimethyl acrylamide), sulfonated polystyrene, or a class of poly(alkylene oxide). These highly hydrophilic synthetic polymers may be modified by other chemical treatments such as cross-linking or hydrolysis. Further examples known in the art are the non-ionic hydrophilic polymers such as polyoxyethylene, polyoxypropylene and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium (or combination of cations), acrylate, may be placed on the absorbing layer by spraying or otherwise placing a solution thereon followed by polymerization and cross-linking, for example, by irradiation.

In addition, naturally occurring materials such as gums, may be used. For instance, guar gum is suitable.

The superabsorbent material is combined with the fibrous web by any means suitable to distribute the superabsorbent material therein trying to minimize interference by one superabsorbent entity with another upon the swelling of the first. If the superabsorbent material is a powder it may be sprinkled onto the fibrous web either in dry form or the web may be moistened. If the superabsorbent is in granular form it may be desirable to slightly moisten the superabsorbent before placing it in contact with the web. The superabsorbent material will contain particles which range in size from about 0.005 mm in diameter to globules that are continuous along fibers for a distance up to several inches.

Another method of placing the superabsorbent in the web is spraying a monomer solution on the web or saturating the web with a monomer solution followed by polymerization of the monomer. One typical way to polymerize the monomer is by use of irradiation. It is desirable to place the superabsorbent somewhat evenly throughout the fibrous web. However, even if the superabsorbent is powderlike and in the form of a layer, it tends to function better than such a layer has in previously known products. It may be desirable to place more superabsorbent in one area than in another and/or to place the superabsorbent in the structure in predetermined patterns.

Any superabsorbent which absorbs large amounts of liquids is suitable for use in the absorbing layer of the present invention.

The fibrous web containing the superabsorbent tends to be stiff and substantially non-flexible. Since the end uses of the fibrous web require that the web be soft, flexible and pliable, it has been discovered that microcorrugation of the fibrous web provides the necessary reduction in stiffness without damaging the properties of the fibrous web which are desirable for its end use. Frequently, the Taber stiffness of a web containing at least 200 percent superabsorbent exceeds 300 Taber stiffness (gm/linear cm) in the machine direction. In the cross-direction, the Taber stiffness generally exceeds 70. In order to have a product satisfactory for use in disposable products, such as diapers and sanitary napkins, it is necessary to reduce the Taber stiffness value to less than about 25. The Taber stiffness value is obtained in accordance with the procedure found at ASTM D 2969. All Taber stiffness values are expressed in gm/linear cm.

The absorbing layer comprised of the fibrous web and superabsorbent may be treated to reduce the Taber stiffness on the layer alone or after the layer has been combined with a wicking layer.

The wicking layer is comprised of hydrophilic fibers, such as rayon fibers, cellulosic fibers, peat moss, acrylic fibers, or mixtures thereof. The cellulosic fibers include wood pulp fibers, cotton linters, and the like. The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers or peat moss or mixtures thereof are placed in such a way as to form a layer in which the particles are close to one another so as to provide a higher capillary pressure to promote wicking of liquid in the plane of the layer.

What appears to be only a small difference in capillary pressure is all that is required for one layer to attract and drain liquid from an adjacent layer. The force causing a liquid to enter a cylindrical capillary is expressed by the equation:

$$P = \frac{(2\nu \cos \theta)}{r}$$

wherein the force is represented by the capillary pressure and

P is the capillary pressure,
$\nu$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones.

The relative wickability between a first fibrous layer and a second layer is affected by both the relative densities of the layers and the relative wettability of the individual fibers in each layer. The individual fibers of the second layer preferably have substantially smaller liquid fiber contact angles than those of the first fibrous layer overcoming the density difference and providing a significant overall increase in capillary pressure to absorb liquid into the second layer.

The fibers of the second layer of fibers (or particles) and/or the density of the layer are selected to create a significant difference in capillary pressure from the first fibrous layer.

The second fibrous (or particle) layer is generally comprised of fibers having a lower liquid-contact angle or wherein the layer is provided with a narrower capillary radii. Examples of such fibers include hydrophilic fibers such as rayon fibers, cellulosic fibers, or peat moss, or mixtures thereof, or acrylic fibers, or the like. Cellulosic fibers include wood pulp fibers, cotton linters and the like.

The wicking layer can be preformed and placed next to the absorbing layer before compression or the wicking layer particles can be air-laid, mechanically entangled therewith, or wet-laid on to the absorbing layer before compression.

The transition zone is a region formed at the junction of the absorbing layer and the wicking layer. Some of the particles, e.g., fibers, of the wicking layer extend into and become integral with the absorbing layer. The region in which the majority of the extending particles lie is identified as the transition zone. In the transition zone, there is a composite of absorbing layer fibers, superabsorbent material, and wicking layer particles. The wicking layer particles which have extended into the absorbing layer are in intimate contact with some of the superabsorbent material of the absorbing layer. This permits the liquid to commence its migration in the z direction to reach the superabsorbent material. As the liquid progresses in the z direction, the superabsorbent material becomes soft and releases the absorbing layer fibers which permit the absorbing layer to return substantially to its uncompressed thickness or more. As the absorbing layer returns to its uncompressed thickness, larger void areas are provided for storage of the liquid and for increased swelling of the superabsorbent material as it absorbs the liquid residing in the void areas. The absorbing layer tends to return to its uncompressed thickness or more, probably because of both the resiliency of the fibers and the swelling of the superabsorbent material.

In order for the absorbing layer fibrous web to provide the necessary medium for absorbing liquid, it is preferred that the fibrous web has an initial dry bulk of at least about 20 cc/gm, a dry bulk recovery of at least 30 percent, (peferably 50 percent), a wet bulk of at least about 30 cc/gm, and a weight of less than about 4 oz/yd². The initial dry bulk is the area times thickness of the layer under a load of 0.01 pounds per square inch calculated in cubic centimeters. This value is divided by the weight in grams in order to provide the measurement in cubic centimeters per gram. The dry bulk recovery is obtained by subjecting the web to a load of 1.75 psi for five minutes, removing the load and allowing the web to rest for one minute, subjecting the web to a load of 0.01 psi for one minute and then measuring the final dry bulk while under the 0.01 psi load. The dry bulk recovery is the final bulk divided by the initial bulk expressed in percent. The wet bulk is measured in the same manner as the initial dry bulk except that the web has been saturated with water. It has been found that if the fibrous web is provided with a dry bulk recovery of at least 20 percent (preferably 50%), an initial dry bulk of at least 20 cc/gm, a wet bulk of at least 30 cc/gm, with a web weight of less than 4 oz/yd², the fibrous web can retain superabsorbent material up to at least 1,500 percent of the dry basis weight of the web. It is preferable that the web contain 200 percent to 1,500 percent by weight, dry basis, superabsorbent to the dry basis weight of the web and most preferred is a range from about 400 percent to about 1,200 percent.

The means by which the absorbent structure is rendered flexible, pliable, and soft according to the present invention is by utilization of mechanical working. The mechanical working is identified as microcorrugating. The technique of microcorrugatiang is disclosed in U.S. Pat. No. 4,116,892 to Schwarz. Although the technique in this patent is identified as one for stretching fibers in order to orient the fibers, the present invention does not wish to stretch but to mechanically work. Schwarz uses his technique to molecularly orient the fibers in a post molten state. The fibers used in the present invention are already oriented. Thus, additional stretching or further orientation might damage the fibers in the present invention.

It has been discovered that microcorrugating the absorbent structure defined in the present invention puts in hinge lines resulting in a flexible, pliable, soft feel. The rolls described in U.S. Pat. No. 4,116,892 are set with a gap of 0.025–0.30 inch in order to break up the superabsorbent particles to a somewhat uniform size and create the desirable hinge lines described heretofore. If the absorbent structure of the present invention is simply put through rolls as to crush the structure, the product actually becomes stiffer and has a higher Taber stiffness value. The stretch to the fibers of the absorbent structure is less than 10 percent when the microcorrugating is performed.

It has been found desirable to pass the materials through microcorrugating in the machine direction and then to pass the material through rolls with embossing rings in order to microcorrugate in the cross-direction. It is highly desirable to reduce the moisture content of the absorbent structure to less than 10 percent before subjecting it to microcorrugating.

In addition to the tenderizing, softening and improved flexibility of the product, it has been noted that the product absorbs liquid more rapidly than prior to the mechanical working treatment. The quick absorption of liquid is particularly beneficial in a disposable diaper product.

Examples of methods of preparing the absorbent structure of the present invention are as follows. These examples are not intended to be limiting in any way and extensions and modifications thereof without departure from the spirit and scope of the invention will become apparent from these examples.

EXAMPLE 1

An absorbing layer is formed of polyester fibers by dry-laying the fibers, i.e., by air-laying or carding the fibers to form a web. Specifically, the polyester fibers contain a minor proportion (about 15 percent) of fusible fibers which soften at a lower temperature than the rest of the fibers. The web is heat bonded by passing air at a temperature of 350° F. through the web for about 10 seconds. The resulting web is about 25 gm/sq. meter basis weight. The specific polyester fibers used are identified as Type 99 Hollofil fibers manufactured and sold by E. I. DuPont Company. The polyester web is coated by flooding it with an aqueous solution of sodium acrylate and acrylic acid. The solution contains 38 percent solids. Excess solution is removed from the web and the web is then subjected to electron beam radiation, in order to polymerize the sodium acrylate to polysodium acrylate. The web is repeatedly flooded with liquid, the excess liquid removed and subjected to irradiation until the amount of dry solids add-on of the polysodium acrylate is 10 times the weight of the web. The coated substrate is passed beneath a Hammermill that deposits wood pulp fibers on to the polyester web. Vacuum is applied under the polyester web so as to lightly compact the wood pulp fibers on to the web. The wood pulp fibers are present in an amount of 50 gm/sq. meter. The surface of the pulp layer is sprayed with water so that the total moisture content of the pulp is about 10 percent by weight. The total structure is compressed at a level of 640 psi for 30 seconds. Upon release of the pressure, the pulp has formed into a high density layer with a capillary size suitable for liquid wicking and the resilient fiber layer remains compressed. The sample when dried to 6 percent moisture has a Taber stiffness of about 158. This stiffness does not permit use of the absorbent structure in products such as disposable diapers and santiary napkins. Addition of moisture up to about 28 percent softens the product to a Taber stiffness of about 75. However, it still is not sufficiently soft and flexible to be used in a disposable diaper product. Furthermore, it is desirable for the absorbent structure to be substantially dry when used in a product so that it can absorb its full capacity of liquid when being used. Upon redrying the product after bringing the moisture to 28 percent, the product at 3 percent moisture has a Taber stiffness value of 119 and at 0 percent moisture has a Taber stiffness value of 145.

Another sample is dried to 6 percent moisture and subjected to microcorrugating rolls first through a pair of intermeshing rolls with a corrugating pattern in the cross-direction followed by passing the sample through an embossing roll with rings that create lines in the machine direction. The resulting Taber stiffness value is about 21 in the machine direction. When this sample is moisturized to about 28 percent, the Taber stiffness value drops to about 13. When the sample is redried to 3 percent and 0 percent moisture, the Taber stiffness values are about 21 and 22, respectively. This clearly shows that by drying the sample before microcorrugating, the microcorrugating is permanent and the sample will remain soft and flexible whether or not it is moisturized and subsequently dried. When a sample is microcorrugated a second time in each direction, the Taber stiffness values are as follows: at 6 percent moisture—11, at 28 percent moisture—10, redried to 3 percent moisture—21, redried to 0 percent moisture—23. A Taber stiffness value below about 50 produces a satisfactory product but the preferred value is less than about 25.

EXAMPLE 2

A polyester nonwoven fibrous web is prepared which contains 67 percent Hollofil fibers and 33 percent Enka fibers. The Enka fibers are a bicomponent fiber having a polyethylene sheath and a polyester core. These fibers are produced and sold by American Enka. The fabric has a weight of 1.2 oz/sq. yd. In a similar procedure to that in Example 1, the polysodium acrylate is placed on the fibers in an amount of dry solids add-on of 10 to 1. The final weight of the superabsorbent containing polyester web is about 12 oz/sq. yd. After formation of the web, approximately 4 oz/sq. yd. on each side of the web of wood pulp fibers are deposited and the web is compressed. When dried to a moisture level of 3 percent, the web exhibits a Taber stiffness of 343 gm/cm. in the machine direction and 75.8 gm/cm. in the cross-direction. Samples of the web (10 inches × 15 inches), are dried at 375° F. to a moisture content of 3 percent. The samples are then processed through the microcorrugating rolls in the machine direction. The rolls are 7 inch cylinders having microcorrugated peaks at 30 dp (diametral pitch) with an engagement of 0.04 inch at a pressure of 290 pounds per lineal inch. The samples are then placed through the embossing rolls with rings to microcorrugate the product in the cross-direction. These samples after microcorrugation have a Taber stiffness value of 26.5 in the machine direction and 15 in the cross-direction. The microcorrugated samples reveal a higher absorption of liquid and a more rapid absorption of liquid as shown in FIG. 10. The wicking ability of the microcorrugated product is substantially equal that of the product prior to microcorrugating. Thus, the mechanical working by microcorrugation has not interfered with the ability of the product to wick liquid from one region of the product to another. This is very important in a structure such as a disposable diaper.

Other variations of the methods for preparing the absorbent structure of the present invention may be used.

From the foregoing, it will be observed that numerous variations and modifications may be effected without departing from the true spirit and scope of the novel concept of this invention.

I claim:

1. An absorbent structure comprising a fibrous web of resilient fibers, said web having a basis weight less than about 4 oz/sq. yd., an initial dry bulk of at least about 20 cc/gm., a dry bulk recovery of at least about 30 percent and a wet bulk of at least about 30 cc/gm., and superabsorbent disposed in amongst the fibers of said web in an amount of at least about 200 percent by weight based on said web weight, said structure having a Taber stiffness value less than about 50.

2. The absorbent structure of claim 1 wherein said Taber stiffness value is less than about 25.

3. The absorbent structure of claim 1 wherein a layer of wood pulp fibers has been placed on at least one side of said absorbent structure.

4. The product of claim 3 wherein a layer of wood pulp fibers is placed on both sides of said absorbent structure.

5. The absorbent structure of claim 1 wherein said fibrous web is a web of polyester fibers.

6. A disposable diaper containing as the absorbing layer an absorbent structure comprising a fibrous web, said we having of at least about 20 cc/gm., a dry bulk recovery of at least about 30 percent, and a wet bulk of at least about 30 cc/gm., and superabsorbent disposed in amongst the fibers of said web in an amount of at least about 200 percent by weight based on said web weight, said structure having a Taber stiffness value less than about 50.

7. A sanitary napkin having as the absorbent layer an absorbent structure comprising a fibrous web having a basis weight less than about 4 oz/sq. yd., an initial dry bulk of at least about 20 cc/gm., a dry bulk recovery of at least 30 percent, and a wet bulk of at least about 30 cc/gm., and superabsorbent disposed in amongst the fibers of said web in an amount at least about 200 percent by weight based on said web weight, said structure having a Taber stiffness value less than about 50.

8. A method for preparing an absorbent structure being capable of absorbing at least about 5 cc/gm. of liquid and being a nonwoven web having a basis weight of less than about 4 oz/sq. yd., an initial dry bulk of at least about 20 cc/gm., a dry bulk recovery of at least about 30 percent, and a wet bulk of at least about 30 cc/gm., said web containing at least about 200 percent by weight superabsorbent comprising:
 (a) drying said web containing superabsorbent to a moisture content less than about 25 percent, and
 (b) microcorrugating said web to provide a Taber stiffness of less than about 50.

9. The method of claim 8 wherein said Taber stiffness value is less than about 25.

10. The method of claim 8 wherein said Taber stiffness value is less than about 10 in at least one direction.

* * * * *

UNITED STATES PATENT AND TRADEMARK OFFICE
CERTIFICATE OF CORRECTION

PATENT NO. : 4,559,050

DATED : December 17, 1985

INVENTOR(S) : Michael J. Iskra

It is certified that error appears in the above-identified patent and that said Letters Patent is hereby corrected as shown below:

Claim 6, line 4: "said we" should read --said web--.

Signed and Sealed this

Second Day of December, 1986

Attest:

DONALD J. QUIGG

Attesting Officer      Commissioner of Patents and Trademarks